Figure 1:
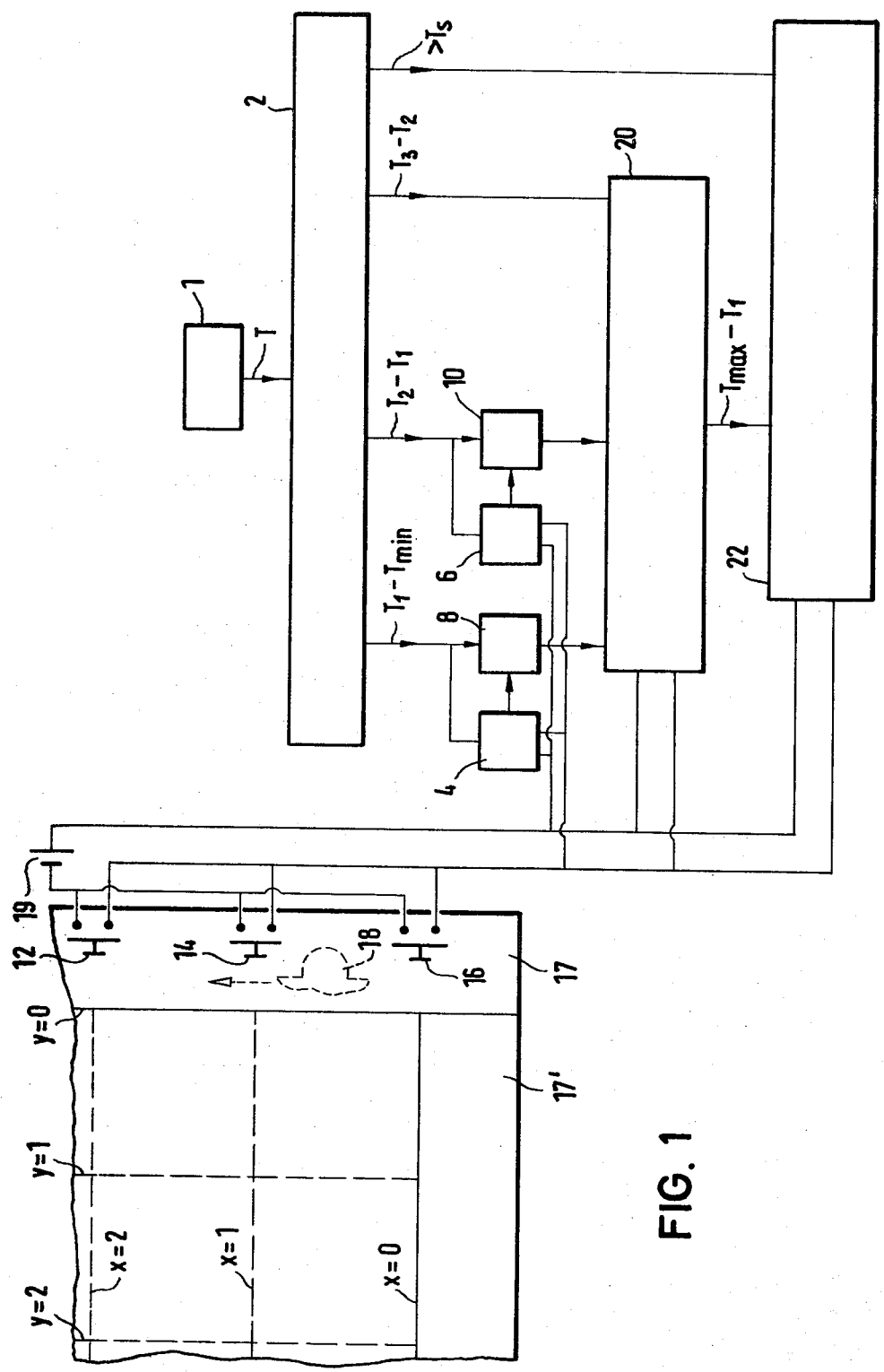

United States Patent [19]

Karlsson

[11] 4,138,277

[45] Feb. 6, 1979

[54] METHOD AND APPARATUS FOR PRODUCING METAL BLANKS, IN PARTICULAR STEEL SLABS, WHICH AT LEAST IN A PREDETERMINED SURFACE AREA HAVE SUBSTANTIALLY NO DEFECTS

[75] Inventor: Per-Olle Karlsson, Oxelösund, Sweden

[73] Assignee: Granges Oxelösunds Jarnverk AB, Sweden

[21] Appl. No.: 677,078

[22] Filed: Apr. 15, 1976

[30] Foreign Application Priority Data

Dec. 29, 1975 [DE] Fed. Rep. of Germany ....... 2558966

[51] Int. Cl.$^2$ ................................................. B23K 7/06
[52] U.S. Cl. ........................................ 148/9.5; 266/51; 324/57 R
[58] Field of Search ............................ 148/9.5; 324/57; 266/51

[56] References Cited

U.S. PATENT DOCUMENTS

| | | | |
|---|---|---|---|
| 3,593,120 | 7/1971 | Mandula, Jr. et al. | 324/37 |
| 3,609,531 | 9/1971 | Förster | 324/37 |
| 3,657,638 | 4/1972 | Höller et al. | 324/37 |
| 3,676,959 | 7/1972 | Förster | 324/37 |
| 3,822,632 | 7/1974 | Chigiotti | 148/9.5 |
| 3,967,193 | 6/1974 | Bergstrand | 324/37 |

*Primary Examiner*—W. Stallard

*Attorney, Agent, or Firm*—Craig & Antonelli

[57] ABSTRACT

Method and apparatus for producing metal blanks, in particular steel slabs, which at least in a predetermined surface area have substantially no defects such as cracks, seams, bubbles, scabs, or the like, at least the surface portion to be made free of defects being systematically and substantially completely scanned by means of at least one inspecting device which detects such defects at and closely beneath the surface as regards location and depth and a working means being controlled by means of the recorded defects, which by scarfing, grinding, milling, planing and/or another cutting machine and/or local material melt deposition and/or material replacement or the like removes the defects detected, the defects being recorded with their depth for surface sub-areas whose width transversely of the working means is sustantially equal or less than the smallest working width of the working means and the working depth of the working means being controlled in accordance with the maximum defect depth recorded for the particular surface sub-area to be worked, wherein defects which occur within a surface sub-areas in a defect accumulation exceeding a predetermined defect minimum number and/or defects having a longitudinal extent whose direction deviates appreciably from the rolling direction are especially marked and/or taken into account with a weight changed with respect to a single defect in the determination of the maximum defect depth.

17 Claims, 2 Drawing Figures

METHOD AND APPARATUS FOR PRODUCING METAL BLANKS, IN PARTICULAR STEEL SLABS, WHICH AT LEAST IN A PREDETERMINED SURFACE AREA HAVE SUBSTANTIALLY NO DEFECTS

The invention relates to an improvement of the copending application Ser. No. 591,937 relating to a method and apparatus for producing metal blanks, in particular steel slabs, which at least in a predetermined surface area have substantially no defects such as cracks, seams, bubbles, scabs or the like. In the application Ser. No. 591,937 it is suggested that by such method the surface portion of the slab to be made free of defects is divided by means of a preferably right-angle coordinate system into sub-areas and systematically and substantially completely scanned by an inspecting device detecting such defects at and closely beneath the surface and recording such defects divided according to their depth in a plurality of depth classes, and in which the maximum defect depth or the maximum defect depth class detected for the particular surface sub-area will control the working depth of the working means to remove the defects detected by scarfing, grinding, milling, planing, and/or another cutting machine and/or local material melt deposition and/or material replacement or the like.

It has been found that in particular when using electrical, magnetic and/or magnetic-inductive inspection means, in particular eddy current inspection means, although all cracks which emerge in line form at the slab surface and extend perpendicularly into the material are indicated substantially with the correct depth, other types of defects, such as bubbles, scabs or the like are frequently not indicated and recorded with the correct depth.

The problem underlying the present invention is to improve the method according to the parent patent or parent patent application so that as far as possible all types of defects are detected and recorded with the correct depth and the defects detected can be completely removed without excess loss of material or excess expenditure on machining.

According to the invention this problem is solved in that defects which occur within a coordinate field and/or within two adjoining coordinate fields in an accumulation exceeding a predetermined defect minimum number and/or defects having a longitudinal extent whose direction deviates appreciably from the rolling direction are especially marked and/or taken into account with a weight changed with respect to a single defect in the determination of the maximum defect depth or maximum defect depth class.

The method according to the invention has the advantage that signals of defect types which with electrical, magnetic and/or magnetic-inductive inspection means, in particular eddy current inspection means, are generally indicated with a signal magnitude which does not correspond to their true depth can be especially marked and/or corrected in such a manner that the depth of these types of defect is also correctly recorded.

The depth of crack defects which appear at the slab surface in line form and extend from the slab surface perpendicularly into the material is generally correctly indicated when using electrical, magnetic, magnetic-inductive and eddy current inspection means. However, when using such inspection means the depth of defects which are distributed in area manner or extend over an area is generally indicated with a signal magnitude which does not correspond to the true depth. Defects distributed or extending over an area are referred to hereinafter as "area" defects to distinguish them from line-form defects.

"Area" defects occur in continuously cast slabs in the form of bubble formations and/or macro-slags and in rolled slabs as scab formations or as socalled "cork surfaces". The latter "cork surfaces" are frequently due to bubble formations, the bubbles lying near the slab surface being opened by the rolling operation and in many cases scale layers or scale particles being rolled in. "Cork surfaces" may however also occur with slag inclusions.

A further type of defect whose depth is also generally indicated erroneously when using the aforementioned inspection means is crack defects extending obliquely from the slab surface into the interior of the material. Such crack defects occur in rolled slabs when a crack running transversely of the rolling direction and originally extending perpendicularly from the slab surface into the material is given an inclination to the slab surface by the rolling operation so that said crack extends after the rolling from the slab surface in inclined manner into the interior of the material. In the case of rolled slabs, all cracks running transversely of the rolling direction extend after the rolling, as a result of the rolling operation, obliquely from the slab surface into the interior of the material. Hereinafter these cracks are also referred to as "inclined" cracks or "inclined" defects.

In contrast, no inclination to the slab surface is imparted by the rolling operation to cracks which run substantially parallel to the rolling direction. Consequently, after the rolling operation as well these cracks extend generally perpendicularly to the slab surface into the material and consequently are generally indicated with the correct depth by the inspection means mentioned at the beginning.

To enable a distinction to be made between the "inclined" cracks extending transversely of the rolling direction and those which extend parallel to the rolling direction and are not given an inclination to the slab surface by the rolling operation, according to the invention the cracks extending parallel to the rolling direction and the cracks extending transversely of the rolling direction are detected separately, preferably by means of separate inspection means, in such a manner that the signals of these two types of defects can be distinguished from each other and a correction may be made for the "inclined" cracks running transversely of the rolling direction and extending from the slab surface obliquely into the interior of the material.

The method according to the invention makes it possible to distinguish between various types of defects, for example (a) line-form crack defects extending from the slab surface substantially perpendicular into the material (b) "area" defects and (c) so called "inclined" defects extending from the material surface obliquely into the interior of the material and to mark them separately and/or to take account of the signals obtained from the various types of defects with a different weight in the determination of the defect depth.

The defects which are generally not indicated with the correct depth when using the inspection means mentioned at the beginning include those which are covered partially or completely by a thin surface layer. Such so called "concealed" defects generally occur after the annealing of the slab surface at the latter if the defects are covered by a surface layer which is so thin that during the annealing of the slab said layer is oxidized and is removed as scale layer. The thickness of the surface layer of the slab which is converted to a scale layer during annealing depends on the material and the annealing process and depending upon the annealing process may for example be between 2 mm and 5 mm and in particular 3 mm. This scale layer which is formed during the annealing may however also be substantially thinner and in particular in the case of heat-resistant steels and stainless steels practically non-existent. Cracks which are covered by a surface layer which is thicker than the surface layer oxidized on annealing to a scale layer generally do not have a negative effect on the material rolled because even during the annealing they do not come into contact with the atmosphere and the material in the region of such non-oxidized cracks is intimately bonded again by the rolling operation, a sort of "welding together" of the material taking place.

It has now been found that such "concealed" defects generally occur in aggregations and represent "area" defects which in the respective coordinate field produce a great number of defect pulses. Such "concealed" defects are frequently also due to bubble formations, inclusions of macro-slags or the like, said bubble formations, macro-slags or the like being covered by a thin surface layer. Due to the thin surface layer, the "concealed" defects generally give defect signals which are too small when using electrical, magnetic, magnetic-inductive and eddy current inspection means.

With the method according to the invention the defects determined are classified in various depth classes, for example all defects up to a depth $T_1$ in a first depth class, all defects up to a depth greater than $T_1$ and smaller or equal to $T_2$ in a second depth class and all defects with a depth greater than $T_2$ and smaller or equal to $T_3$ in a third depth class and all defects with a depth greater than $T_3$ in a fourth depth class.

The first depth class, which usually does not require any machining of the slab, includes substantially the single defects which are indicated with a depth which is substantially equal to or less than the thickness of the scale layer produced on annealing of the slab, e.g. about 3 mm or less.

To enable a correction to be made for the previously mentioned "concealed" defects which are generally indicated with a defect signal which is too small, it is advantageous according to the invention in the case of defects which are indicated with a depth which is so small that they would normally be put into the first depth class not requiring machining of the slab to take account of these defects when they occur in aggregations and classify them in a defect depth class requiring machining of the slab.

However, according to the invention it is advantageous in the case of defect accumulations to take account of the defects indicated with a depth lying in the aforementioned first depth class with a weight modified with respect to a single defect only in so far as the indicated defect depth is above a minimum or threshold value, preferably 0.5 to 1 mm. Advantageously, this minimum or threshold value is selected to be above the defect depths which are indicated due to the usual surface nature or surface roughness of a slab which is in itself free from defects.

It may be advantageous to supply the defects indicated in various depth classes to separate counting means to determine defect accumulations — separated in depth classes. In the various defect depth classes different defect minimum numbers, preferably between four and ten defects, may serve as criterion for a defect accumulation, said defect minimum numbers of the separate counting means preferably being adjustable to permit adaptation to definite defect types and/or slab types and/or material types. Furthermore, according to the invention in the case of defect accumulations or aggregations the indicated defect depths — separated in defect depth classes — are taken into account with different weight during the determination of the maximum defect depth or maximum defect depth class. Advantageously, in this respect as well a variable adjustment of the weights and thus an adaptation to different types of defect, slab and/or material is possible.

It may also be advantageous to count in a common counter the defects indicated in all depth classes for a coordinate field or two adjacent coordinate fields and when a predetermined defect minimum number is exceeded mark the respective coordinate field or fields, for example by means of an ink marking means, and/or to take account of all defects or alternatively only defects in certain depth classes with a modified weight.

It may also be advantageous to use the aforementioned common counter in combination with individual counters for one or more depth classes to enable a better distinction to be made between various types of defects and thus to take account of them with improved adaptation of their weight.

To enable various types of defects to be separated from each other in improved manner it may also be advantageous to use one or more counters which produce signals on reaching two or more preferably adjustable defect minimum numbers, for example at eight and at thirty defects, which may be used to change the weight with which the defects are taken into account when a defect minimum number is exceeded.

Since the partially or completely concealed "area" defects, which frequently occur as so called "cork" defects after the annealing, often have depths up to 10 or 20 mm and such defects, in particular when using eddy current inspection means, are often indicated only with depths which come in the first depth class normally not requiring any machining, it may be expedient to provide such "area" defects always with a weight which is so high that they are classified in the defect depth class requiring the maximum machining depth, for example about 20 mm. This makes it possible to ensure with great probability that the aforementioned "area" defects are completely removed. To increase the certainty, according to the invention it may also be advantageous to work in the same manner the coordinate fields which immediately adjoin a coordinate field in which a defect accumulation has been detected. Since the aforementioned "area" defects generally extend over a surface area having a diameter greater than about 5 cm or more and have an irregular inner structure, they always give an accumulation of defect indications in a coordinate field whose side lengths are generally chosen between 5 and 20 cm, preferably about 10 cm. It is of course advantageous to take account only of those defect indications which lie above the aforementioned minimum or threshold value. To detect as completely as possible partially or completely concealed defects lying beneath the surface even when using eddy current inspection means, according to the invention in such eddy current inspection means excitation frequencies are used of about 200 c/s or less, in particular about 100 c/s or less, preferably however 50 c/s or less. With such low excitation frequencies even defects covered by relatively thin electrically conductive metal layers are still indicated although with a low and falsified depth, which can be taken into account according to the invention.

In the case of continuously cast slabs which have not been subjected to a rolling operation prior to the inspection and thus do not have the aforementioned "inclined" crack defects, according to the invention it may be particularly advantageous to employ an eddy current inspection means with which all defects, in particular also elongated cracks, are reliably indicated with the correct depth independently of the direction of their longitudinal extent to the travelling direction of the inspection means. According to the invention such an eddy current inspection apparatus may comprise two inspection means arranged at an angle of $+45°$ and $-45°$ to the travelling direction of the inspection apparatus or two groups of inspection means, one group of inspection means being disposed at an angle of $+45°$ and the other group at an angle of $-45°$ obliquely to the travelling direction of the inspection apparatus. Such an arrangement of the inspection means also permits indication of elongated cracks or similar defects coinciding directly with the travelling direction without requiring any oscillation movement of one of the inspection means or one group of the inspection means. However, it must be ensured that the inspection means have a substantially constant sensitivity at least over the area of their longitudinal extent in the direction $+45°$ or $-45°$ used for the measurement, which can be achieved by suitable construction and arrangement of the inspection means, in particular when the inspection means consists of correspondingly constructed and arranged measuring coils or combinations of several measuring coils.

Figure 2:
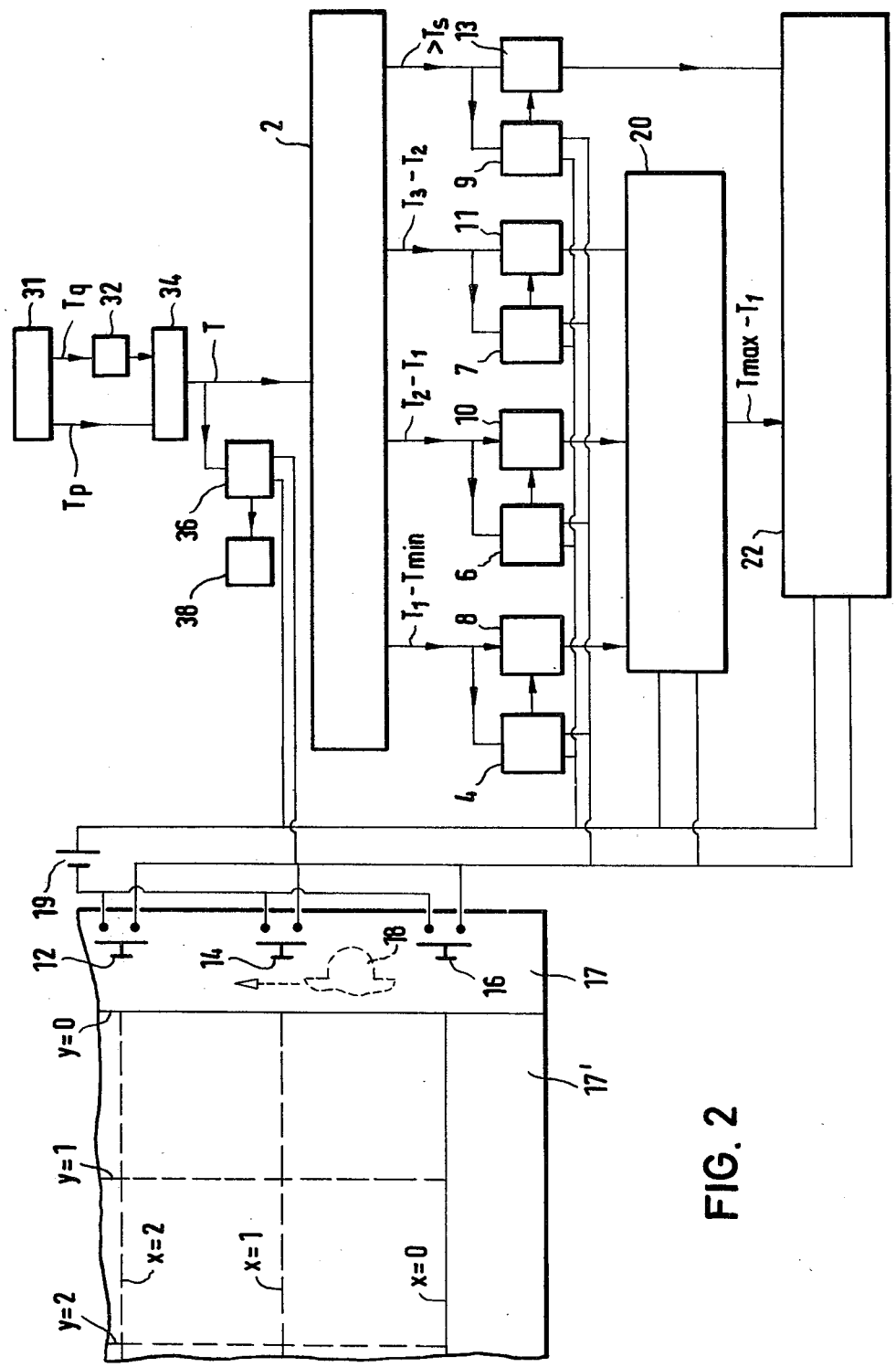

Hereinafter the invention will be explained with the aid of a schematic illustration of examples of embodiment, wherein:

FIG. 1 is a circuit diagram of an apparatus for carrying out the method according to the invention and FIG. 2 is a modified embodiment of the circuit according to FIG. 1.

In FIG. 1 an eddy current inspection apparatus is designated by 1 and emits defect signals T to a classifying means 2, the magnitude of the amplitude of the defect signals T depending on the defect depth. In the classification means 2 the defect signals are separated into four groups, i.e.:

1. Defects with a depth between $T_{min}$ and $T_1$, $T_{min}$ being minimum or threshold value which serves to suppress those defects which are indicated due to the usual surface roughness of a non-defective slab, e.g. $T_{min} = 1$ mm, and $T_1$ being the maximum defect depth which normally requires no after-machining and in particular is obviated by the annealing process as scale layer; e.g. $T_1 = 3$ mm.

2. Defects having a depth between $T_1$ and $T_2$; $T_2$ may for example be equal to 12 mm.

3. Defects with a depth between $T_2$ and $T_3$; $T_3$ may for example be equal to 21 mm.

4. Defects with a depth greater than $T_S$, $T_S$ preferably being made equal to $T_3$.

The signals of the first two depth classes are fed in each case to a counter 4 and 6 respectively and to a means 8 and 10 changing the weight of the defects, said means storing the defect signals until the inspection apparatus has completely travelled over the respective coordinate field.

However, this means changing the weight of the defects is effective only when the associated counter has reached the respective set minimum defect number within a coordinate field. The counters 4 and 6 are reset to zero by pulse generators, preferably microswitches 12, 14, 16 when the inspection means 1 moves over the boundary of a coordinate field. The number of pulse generators 12, 14, 16 depends on the number of coordinate fields into which the slab surface is divided transversely of the travelling direction of the inspection means, the pulse generators 12, 14, 16 etc. being fixedly mounted preferably at the stop bar 17 for the end face of the slab with a mutual spacing which corresponds to the side length of a coordinate field in the travelling direction, e.g. 10 cm. The pulse generators 12, 14, 16 may thus be constructed as microswitches which are briefly closed by an actuating cam 18 indicated in dashed line and fixedly connected to the inspection apparatus 1 to produce switch impulses in conjunction with a voltage source indicated at 19.

As is apparent from the drawings, the pulse generators 12, 14, 16 are disposed on the end-face stop bar 17 in each case in an extension of an x coordinate, the coordinate $x = 0$ being formed by the stop edge of a stop bar 17' which bears against the slab longitudinal side. The defect depth signals possibly intensified by the means 8 and 10 are fed to a maximising means 20 which forms the maximum for each coordinate field from the defect depth signals supplied thereto. In the maximising means 20, however, all defect depth signals smaller or equal to $T_1$ are suppressed so that the signals of the first class $T_1$-$T_{min}$ are taken into account only when their weight is increased by the means 8 beyond $T_1$. The maximising means 20 is preferably so designed that it does not pass the value $T_{max}$ onto a following signal storage and control means 22 but the value $T_{max}$ - $T_1$. Said signal storage and control means 22 stores the values $T_{max}$ - $T_1$ supplied thereto with the particulars of the respective coordinate field for the control of the machining means, $T_1$ being selected according to the invention substantially equal to the thickness of the material layer which is eliminated on annealing of the slab as scale layer. If however a signal greater than $T_S$ is supplied to the storage and control means 22 the slab is classified as waste as described in detail in applicant's copending applications Ser. Nos. 591,937 and 591,938.

The counters 4 and 6 are preferably set to a minimum defect number between 5 and 10 so that on reaching said minimum defect number they pass on a signal to the means 8 and 10 changing the weight of the defects to render said means 8 and 10 operative. In one example of embodiment in which $T_{min} = 1$ mm, $T_1 = 3$ mm, $T_2 = 12$ mm and $T_3 = 21$ mm, the means 8 increased the weight of the defects when an accumulation thereof was present by a factor of 4 so that in the case of a defect accumulation of the defects lying in the first defect class $T_1 - T_{min}$ said defects were elevated to defects of the second class $T_2 - T_1$; the means 10 were so set that in the case of a defect accumulation of the defects determined in the second class $T_2 - T_1$, i.e. on activation of the means 10 by the counter 6, the defects of the second class were increased by the factor 1.75 so that said defects were taken into account in the third class in so far as they are indicated by the inspection means 1 with a signal which is above about 6.86 mm. In a modified example of embodiment the means 8 was set so that it effected an increase in the weight by the factor 7 and as a result with a defect accumulation in the first defect class the defects of the first class were also taken into account as defects of the third class which were indicated by the inspection means with a signal corresponding to a defect depth between about 1.7 mm and 3 mm. To ensure that account was taken of defect accumulations which lie on both sides of an x coordinate due to the resetting of the counters 4 and 6 by the pulse generators 12, 14 and 16 on travelling over an x coordinate, it may be expedient to arrange a second set of pulse generators in each case half way along between adjacent pulse generators 12, 14, 16, i.e. at the x coordinate values $x = 0.5$, $x = 1.5$, $x = 2.5$, etc. Associated with this second set of pulse generators are additional counters which are connected in the same manner as the counters 4 and 6 to the classification means 2 to reliably detect defect accumulations on both sides of the x coordinates $x = 1$, $x = 2$, $x = 3$, etc. These additional counters are connected so that on detection of a defect accumulation in an area between coordinates $x = 0.5$ and $x = 1.5$ or $x = 1.5$ and $x = 2.5$ etc., they effect a change in the weight of the respective defect signals for the two coordinate fields each half covered by the respective area. Advantageously, an intermediate storage means is connected in front of the maximising means 20 which stores the values determined in a coordinate field until the values of the aforementioned additional counters are available, i.e. until the inspection apparatus has travelled forwards half a coordinate field in the scanning direction beyond the respective coordinate field. The intermediate storage means are constructed analogously with the means 8, 10 so that they can change the weight of the signals. The circuit is designed so that the intermediate storage means change the weight of the signals only when the preceding means 8 and 10 for the respective coordinate field defined by integral x coordinates have not effected any change in the weight. Whilst the counters 4 and 6 on resetting to zero emit a pulse to the means 8 and 10 respectively which terminates the storage of the signals and effects their passing on, the corresponding pulse for the intermediate storage means is supplied by the additional counters.

In the example of embodiment according to FIG. 2 all the parts which have not been changed with respect to the example of embodiment of FIG. 1 are provided with the same reference numerals as in FIG. 1. In the the example of embodiment according to FIG. 2, instead of the inspection apparatus 1 shown in FIG. 1 a modified inspection apparatus 31 is provided. Said apparatus 31 comprises two outputs; at the one output defect signals $T_p$ of defects extending substantially parallel to the rolling direction are emitted and at the second output defect signals $T_q$ of defects extending transversely of the rolling direction. Such an inspection apparatus 31 may be an eddy current inspection means comprising for example two sensing coils, each sensing coil having a receiving winding and an energising winding. The receiving windings and the energising windings may be made rectangular, the energising windings being flat and arranged at a slight space above the slab surface to be inspected and the receiving windings being disposed vertically upright in each case within the associated energising winding. In these sensing coils the energising winding axis extends perpendicularly to the slab surface and the axis of the receiving winding extends parallel to the slab surface. Such sensing coils show a pronounced dependence of the magnitude of the measuring signal on the angular position of the receiver winding relatively to the direction of the longitudinal extent of the defect, especially when the energising winding is constructed as elongated rectangle, in the measurement of elongated defects. In the case of sensing coils oscillating parallel to the slab surface a maximum defect indication results when the receiver winding is aligned parallel to the longitudinal extent of the defect. Thus, if two sensing coils are arranged so that the receiver winding of the one is parallel and of the other is perpendicular to the rolling direction cracks running parallel and transversely of the rolling direction are substantially separated from each other. The sensing coil whose receiver winding extends parallel to the rolling direction is oscillated perpendicularly and the sensing coil whose receiver winding extends perpendicularly to the rolling direction is oscillated parallel to said direction.

With the means 32 the weight of the defect signals $T_q$ of defects extending transversely of the rolling direction can be changed. When inspecting rolled slabs it has been found that cracks extending transversely of the rolling direction after the rolling operation extend from the slab surface obliquely to the interior of the material, representing the so called "inclined" cracks, are generally indicated with a defect signal which is too large so that in the means 32 the weight with which these defects are taken into account is generally reduced.

For defects whose longitudinal extent is neither parallel to the rolling direction nor perpendicular thereto but at an angle, for example 45° to the rolling direction, the inspection apparatus 31 usually supplies both a signal $T_p$ and a signal $T_q$. These two components of a defect extending at an angle to the rolling direction must of course be combined in suitable manner in order to record the defects which extend at an angle to the rolling direction with their correct depth. The means 34 serves to combine these two components. Since a crack extending at an angle, for example 45° to the rolling direction is also given an inclination to the slab surface due to the rolling operation, this inclination not however being so pronounced as with a crack extending perpendicularly to the rolling direction, it is expedient for only the component $T_q$ of a crack extending at 45° to the rolling direction to be corrected by the means 32.

The signals T coming from the means 34 are set to a counter 36 and to the classifying means 2. A marking means 38 is actuated when the counter 36 reaches a predetermined adjustable mininum defect number. It may be expedient not to supply all the defect signals T to the counter 36 but by using a means wich is not illustrated to suppress the defect signals lying below the minimum or threshold value $T_{min}$ in such a manner that only the defect signals $T-T_{min}$ are supplied to the counter 36. The means 38 may be constructed as ink marking means which colour the respective coordinate field. Deviating from the example of embodiment of FIG. 1, in FIG. 2 a counter 7 and 9 respectively is provided for the signals coming in the third depth class $T_3-T_2$ and for the signals coming in the fourth depth class. The means 11 and 13 changing the weight of the signals are associated with the counters 7 and 9 and become operative as soon as the counters 7 and 9 have reached the respective predetermined defect minimun number. In particular with non-concealed "area" defects lying exposed at the slab surface defect signals are frequently obtained which are too large. With such defects at least the means 11, 13 changing the weight of the defect signals will be set so that they reduce the weight corresponding to the signals supplied thereto.

The counters 4, 6, 7, 9 and 36 may also be constructed so that on reaching two or more different defect minimum numbers in each case they emit a control signal to the marking means or to the means changing the weight, the latter means being so constructed that due to the pulses which the counters emit on reaching the second or further defect minimum number they are adjustable to a different weight so that on reaching the first defect minimum number in a counter a weight of 0.6 for example becomes operative and on reaching the second defect minimum number a weight for example of 0.4. Since it is not until the occurrence of the pulses emitted by the counters 4, 6, 7 and 9 on their resetting to zero and passed to the means 8, 10, 11 or 13 that the signals stored by said means are passed on, the signals are passed on in each case with the weight which corresponds to the highest defect minimum number reached in the respective coordinate field. Analagously, the marking means 38 may be provided with two or more ink spraying means with different colours when the counter 36 is adjustable to two or more defect mininum numbers, the ink marking means possibly being initiated only by a pulse emitted by the counter 36 when the latter is reset to zero and only those ink spraying means being actuated whose colour corresponds to the greatest defect minimum number reached in the respective coordinate field.

What is claimed is:

1. Method for producing metal blanks, in particular steel slabs, which at least in a predetermined surface area have substantially no defects such as cracks, seams, bubbles, scabs or the like, at least the surface portion of the slab to be made free of defects being divided by means of a preferably rectangular coordinate system into coordinate fields and being systematically and substantially completely scanned by means of an inspection means detecting such defects at and closely beneath the surface and dividing them into a plurality of depth classes, and the maximum defect depth or maximum defect depth class determined in each case for a coordinate field being used to control the respective machining depth of a machining means which removes defects by scarfing, grinding, milling, planing and/or another cutting machining and/or local material melt deposition and/or material replacement, characterized in that when using electrical, magnetic and/or magnetic-inductive inspection means, in particular eddy current inspection means, defects which occur within a coordinate field and/or within two adjacent coordinate fields in a defect accumulation exceeding a predetermined defect minimum number are especially marked and/or taken into account with a weight changed with respect to a single defect in the determination of the maximum defect depth or maximum defect depth class.

2. Method according to claim 1, characterized in that defects which are indicated with a depth which is so small that they would normally be put into the first depth class $T_1$ not requiring machining of the slab are also taken into account when they occur in defect accumulations and are classified in a defect depth requiring machining of the slab.

3. Method according to claim 2, characterized in that in the first depth class $T_1$ normally requiring no machining of the slab substantially those individual defects were placed which are indicated with a depth which is about equal to or less than the scale layer forming on annealing of the slab, e.g. about 3 mm or less, and that in the case of defect accumulation the defects indicated with a depth lying in said first depth class $T_1$ are taken into account with a weight changed with respect to a single defect in so far as their indicated defect depth is above a minimum or threshold value $T_{min}$, preferably 0.5 to 1 mm.

4. Method according to claim 3, characterized in that the minimum or threshold value $T_{min}$ is selected above the defect depths which are indicated due to the natural surface nature or natural surface roughness of a slab in itself free from defects.

5. Method according to claim 4, characterized in that the defects indicated in the various defect depth classes are supplied to separate counters to determine defect accumulations as separated in depth classes.

6. Method according to claim 5, characterized in that in the various defect depth classes different defect minimum numbers serve as criterion for a defect accumulation.

7. Method according to claim 6, characterized in that in the case of defect accumulations the indicated defect depths — separated in defect depth classes — are taken into account with different weight in the determination of the maximum defect depth or maximum defect depth class.

8. Method according to claim 1, characterized in that in the case of defect accumulation the defect depths indicated by the inspection means are taken into account in the determination of the maximum defect depth with a weight which is increased with respect to a single defect and which to a first approximation is substantially inversely proportional to the defect depth indicated.

9. Method according to claim 1, characterized in that on detection of a defect accumulation within a coordinate field of machining of said coordinate field is always effected and preferably also of the immediately adjacent coordinate fields with the maximum machining depth.

10. Method according to claim 1, characterized in that in the calculation of the machining depth necessary to eliminate the defects the thickness $T_1$ of the material layer which is converted to a scale layer on annealing of the slab is deducted.

11. Method according to claim 1, characterized in that an inspection means is used which for defects extending substantially in the rolling direction and for defects extending transversely of the rolling direction emits separate defect signals $T_p$, $T_q$ and that the weight of the signals $T_q$ of the defect signals extending transversely of the rolling direction is changed by a means changing the weight.

12. Method for producing metal blanks, in particular steel slabs, which at least in a predetermined surface area have substantially no defects therein, at least the surface portion be made free of defects being divided by a coordinate system into coordinate fields and being systematically and substantially completely scanned by an inspecting means for detecting defects and the depth thereof within respective coordinate fields, classifying the detected defects into a plurality of depth classes, and utilizing the maximum defect depth or maximum defect depth class determined for at least one coordinate field to control the working depth of a working means for removing the detected defects, characterized in the steps of detecting the number of defects and the depth thereof occurring with a coordinate field and/or within two adjacent coordinate fields, and at least one of marking at least a portion of the coordinate field and/or adjacent coordinate fields when the detected number of defects exceeds a predetermined defect mininum number, and changing the weighting accorded to the detected defects with respect to a single defect in the classification of at least one selected maximum defect depth or maximum defect depth class when the detected number of defects of the at least one maximum defect depth or maximum defect depth class exceeds a predetermined minimum number of defects.

13. Method according to claim 12, characterized in the step of changing the weight according to the detected defects with respect to a single defect in the classification of at least one selected maximum defect depth or maximum defect depth class when the detected number of defects of the at least one maximum defect depth or maximum defect depth class exceeds a predetermined minimum number of defects.

14. Method according to claim 13, characterized in that the number of defects for each of a plurality of maximum defect depths or maximum defect depth classes are detected and upon exceeding a predetermined minimum number of detected defects of a respective maximum defect depth or maximum defect depth class changing the weighting accorded to the detected defects with respect to a single defect in the classification of the respective maximum defect depth or maximum defect depth class.

15. Method according to claim 14, characterized in that the predetermined minimum number of detected defects for respective maximum defect depths or maximum defect depth classes are different.

16. Method according to claim 13, characterized in that the inspecting means is an electrical, magnetic and/or magnetic-inductive inspecting means.

17. Method for producing metal blanks, in particular steel slabs, which at least in a predetermined surface area have substantially no defects therein, at least the surface portion be made free of defects being divided by a coordinate system into coordinate fields and being systematically and substantially completely scanned by an inspecting means for detecting defects and the depth thereof within respective coordinate fields, classifying the detected defects into a plurality of depth classes, and utilizing the maximum defect depth or maximum defect depth class determined for a coordinate field to control the working depth of a working means for removing the detected defects, characterized in the steps of detecting defects having a longitudinal extent in a direction which deviates appreciably from the rolling direction of the slab, and weighting the detected defects having the longitudinal extent in the deviating direction, differently than detected defects having a longitudinal extent in the rolling direction, and classifying the detected defects in accordance with the weighting accorded thereto.

* * * * *